United States Patent [19]
Patel et al.

[11] Patent Number: 5,510,510
[45] Date of Patent: Apr. 23, 1996

[54] INHIBITORS OF FARNESYL PROTEIN TRANSFERASE

[75] Inventors: Dinesh V. Patel, Fremont, Calif.; Scott A. Biller, Ewing, N.J.

[73] Assignee: Bristol-Meyers Squibb Company, Princeton, N.J.

[21] Appl. No.: 267,080

[22] Filed: Jun. 28, 1994

Related U.S. Application Data

[63] Continuation-in-part of Ser. No. 240,356, May 10, 1994, abandoned.

[51] Int. Cl.$^6$ .................................................. C07C 69/02
[52] U.S. Cl. ...................... 560/129; 560/147; 560/155; 560/174; 560/179; 560/205; 560/226; 560/312; 562/9; 562/10; 562/11; 562/15; 562/16; 562/23; 562/36; 562/37; 562/41; 562/104; 562/113; 562/126
[58] Field of Search ................................ 560/147, 129, 560/155, 174, 179, 205, 226, 312; 562/9, 10, 11, 15, 16, 23, 36, 37, 41, 104, 113, 126

[56] References Cited

U.S. PATENT DOCUMENTS

| 5,120,812 | 6/1992 | O'Lenick et al. | 528/28 |
|---|---|---|---|
| 5,298,655 | 3/1994 | Anthony et al. | 562/598 |
| 5,326,773 | 7/1994 | deSolms et al. | 514/336 |

FOREIGN PATENT DOCUMENTS

| 0810940 | 8/1974 | Belgium . |
|---|---|---|
| 91305283.3 | 12/1991 | European Pat. Off. . |
| 91311658.8 | 7/1992 | European Pat. Off. . |
| 92202924.4 | 9/1992 | European Pat. Off. . |
| 92202923.6 | 9/1992 | European Pat. Off. . |
| 92305926.5 | 12/1992 | European Pat. Off. . |
| 92305925.7 | 1/1993 | European Pat. Off. . |
| 0534546 | 3/1993 | European Pat. Off. . |
| 92202880.8 | 3/1993 | European Pat. Off. . |
| 01102461 | 4/1989 | Japan . |
| 91/02650 | 10/1991 | WIPO . |
| 93/05958 | 1/1994 | WIPO . |
| 93/06990 | 2/1994 | WIPO . |
| 93/10394 | 5/1994 | WIPO . |
| 93/10330 | 5/1994 | WIPO . |
| 93/10353 | 5/1994 | WIPO . |

OTHER PUBLICATIONS

Yamada, et al. J. Org. Chem 56(14) 4569 (1991).
Ilarionov et al, Farmatsiya (Sofia) (1990) 40(3) 32–8 Abstract.
Kimoto, et al. Nippon Kagaku, Kaishi (1976) (6) 949 Abstract.
Y. Reiss et al., Cell, vol. 62, 81–88, (1990).
M. S. Brown et al., Proc. Natl. Acad. Sci., vol. 89, 8313–8316, (1992).
D. L. Pompliano et al., Biochemistry, vol. 319, 3800–3807, (1992).
P. D. Milano et al., Abstract Paper, Am. Chem. Soc., vol. 203, 1–3, (1992).
J. L. Goldstein et al., The Journal of Biological Chemistry, vol. 266, 15575–15578, (1991).
J. F. Hancock et al., The EMBO Journal, vol. 10, 641–646, (1991).
Y. Reiss et al., The Journal of Biological Chemistry, vol. 266, 10672–10677, (1991).
L. D. Arnold et al., J. Am. Chem. Soc., vol. 109, 4649–4659, (1987).
L. D. Arnold et al., J. Am. Chem. Soc., vol. 107, 7105–7109, (1985).
Y. Reiss et al., Proc. Natl. Acad. Sci., vol. 88, 732–736, (1991).
W. Kazmierski et al., Tetrahedron, vol. 44, 697–710, (1988).
S. L. Moores et al., The Journal of Biological Chemistry, vol. 266, 14603–14610, (1991).
J. B. Gibbs et al., The Journal of Biological Chemistry, vol. 268, 7617–7620, (1993).
N. E. Kohl et al., Science, vol. 260, 1934–1936 (1993).
G. L. James et al., Science, vol. 260, 1937–1942 (1993).
A. M. Garcia et al., The Journal of Biological Chemistry, vol. 268, 18415–18418 (1993).
M. Nigam et al., The Journal of Biological Chemistry, vol. 268, 20695–20698 (1993).
S. L. Graham et al., J. Med. Chem., vol. 37, 725–732 (1994).

*Primary Examiner*—José G. Dees
*Assistant Examiner*—Joseph M. Conrad, III
*Attorney, Agent, or Firm*—John M. Kilcoyne

[57] ABSTRACT

Inhibition of farnesyl transferase, which is an enzyme involved in ras oncogene expression, and inhibition of cholesterol biosynthesis, are effected by compounds of the formula $$R \overset{()}{\underset{m}{\frown}} X_p \overset{()}{\underset{n}{\frown}} Y$$

their enantiomers, diastereomers, and pharmaceutically acceptable salts, prodrugs, and solvates, wherein:

x is $-ONR^1C(O)-$, $-N(OR^1)C(O)-$, $-NR^1C(O)-$, $-C(O)NR^1-$, $-NR^1S(O_2)-$, $-C(O)O-$, $-OC(O)-$, $-C(O)-$, $-O-$, $-NR^1-$ or $-(S)_q-$;

Y is $-CO_2R^2$, $-SO_3R^2$ or $-P(O)(OR^2)(R^3)$;

R is alkyl, substituted alkyl, alkenyl, substituted alkenyl, alkenylene or aryl;

$R^3$ is $-(O)_tR^4$;

$R^1$, $R^2$ and $R^4$ are each independently hydrogen, alkyl, aryl or aralkyl;

m and n are each independently 0 or an integer from 1 to 5;

p and t are each independently 0 or 1; and q is an integer from 1 to 2.

7 Claims, No Drawings

INHIBITORS OF FARNESYL PROTEIN TRANSFERASE

This application is a continuation-in-part of application Ser. No. 08/240,356, filed on May 10, 1994, now abandoned. The entire contents of the parent application are hereby incorporated by reference.

FIELD OF THE INVENTION

This invention relates to compounds that inhibit farnesyl-protein transferase and Ras protein farnesylation, thereby making them useful as anti-cancer agents. The compounds are also useful in the treatment of diseases, other than cancer, associated with signal transduction pathways operating through Ras and those associated with CAAX-containing proteins other than Ras that are also post-translationally modified by the enzyme farnesyl protein transferase. The compounds may also act as inhibitors of other prenyl transferases, and thus be effective in the treatment of diseases associated with other prenyl modifications of proteins. These compounds additionally are useful in inhibiting cholesterol biosynthesis by inhibiting squalene synthetase (synthase), in hypocholesterolemic and antiatherosclerotic compositions and in a method for inhibiting cholesterol biosynthesis and atherosclerosis.

BACKGROUND OF THE INVENTION

The mammalian ras gene family comprises three genes: H-ras, K-ras and N-ras. The Ras proteins are a family of GTP-binding and hydrolyzing proteins that regulate cell growth and differentiation. Overproduction of normal Ras proteins or mutations that inhibit their GTPase activity can lead to uncontrolled cell division.

The transforming activity of Ras is dependent upon localization of the protein to plasma membranes. This membrane binding occurs via a series of post-translational modifications of the cytosolic Ras proteins. The first and mandatory step in this sequence of events is the farnesylation of these proteins. The reaction is catalyzed by the enzyme farnesyl protein transferase (FPT), and farnesyl pyrophosphate (FPP) serves as the farnesyl group donor in this reaction. The Ras C-terminus contains a sequence motif termed a "Cys-Aaa$_1$-Aaa2-Xaa" box (CAAX box), wherein Cys is cysteine, Aaa is an aliphatic amino acid, and Xaa is a serine or methionine. Farnesylation occurs on the cysteinyl residue of the CAAX box (Cys-186), thereby attaching the prenyl group on the protein via a thio-ether linkage.

Squalene synthetase is a microsomal enzyme which catalyzes the reductive dimerization of two molecules of farnesyl pyrophosphate (FPP) in the presence of nicotinamide adenine dinucleotide phosphate (reduced form)(NADPH) to form squalene (Poulter, C. D.; Rilling, H. C., in "Biosynthesis of Isoprenoid Compounds", Vol. I, Chapter 8, pp. 413–441, J. Wiley and Sons, 1981, and references therein). This enzyme is the first committed step of the de novo cholesterol biosynthetic pathway. The selective inhibition of this step should allow the essential pathways to isopentenyl tRNA, ubiquinone, and dolichol to proceed unimpeded. Squalene synthetase along with HMG-CoA reductase have been shown to be down-regulated by receptor mediated LDL uptake (Faust, J. R.; Goldstein, J. L.; Brown, M. S. *Proc. Nat. Acad. Sci. U.S.A.* 1979, 76, 5018–5022), lending credence to the proposal that inhibiting squalene synthetase will lead to an up-regulation of LDL receptor levels, as has been demonstrated for HMG-CoA reductase, and thus ultimately should be useful for the treatment and prevention of hypercholesterolemia and atherosclerosis.

BRIEF DESCRIPTION OF THE INVENTION

In accordance with the present invention, a compound of the formula

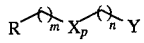

its enantiomers and diastereomers, and pharmaceutically acceptable salts, prodrugs and solvates thereof inhibit S-farnesyl protein transferase, which is an enzyme involved in Ras oncogene function, and inhibit cholesterol biosynthesis. In formula I and throughout this specification, unless otherwise specified, the above symbols are defined as follows:

X is —ONR$^1$C(O)—, —N(OR$^1$)C(O)—, —NR$^1$C(O)—, —C(O)NR$^1$—, —NR$^1$S(O$_2$)—, —C(O)O—, —OC(O)—, —C(O)—, —O—, —NR$^1$— or —(S)$_q$—;

Y is —CO$_2$R$^2$, —SO$_3$R$^2$ or —P(O)(OR$^2$)(R$^3$);

R is alkyl, substituted alkyl, alkenyl, substituted alkenyl, alkenylene or aryl;

R$^3$ is —(O)$_t$R$^4$;

R$^1$, R$^2$ and R$^4$ are each independently hydrogen, alkyl, aryl or aralkyl;

m and n are each independently 0 or an integer from 1 to 5;

p and t are each independently 0 or 1; and q is an integer from 1 to 2.

DETAILED DESCRIPTION OF THE INVENTION

Definition of Terms

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 15 carbon atoms. The expression "lower alkyl" refers to unsubstituted alkyl groups of 1 to 4 carbon atoms.

The expression "substituted alkyl" refers to an alkyl group substituted by, for example, one to four substituents such as halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, N-hydroxycarbamyl, alkoxycarbonyl, phenyl, substituted phenyl, guanidino, indolyl, imidazolyl, furyl, thienyl, thiazolyl, pyrrolidyl, pyridyl, pyrimidyl and the like.

The term "alkylene" refers to a straight chain bridge of 1 to 20 carbon atoms, preferably 1 to 12 carbon atoms, connected by single bonds, which may be substituted by 1 to 5 lower alkyl groups, preferably 1 to 3 lower alkyl groups.

The term "alkenyl" refers to straight or branched chain unsubstituted hydrocarbon groups of 2 to 20 carbons atoms, preferably 2 to 15 carbon atoms, having at least one double bond.

The expression "substituted alkenyl" refers to an alkenyl group substituted by, for example, one to four substituents identified for substituted alkyl.

The term "alkenylene" refers to a straight chain bridge of 1 to 20 carbon atoms, preferably 1 to 13 carbon atoms, having 1 to 5 double bonds, preferably 1 to 3 double bonds, which may be substituted by 1 to 5 lower alkyl groups, preferably 1 to 3 lower alkyl groups. Exemplary alkenylene groups are: farnesyl and geranyl.

The term "halogen" or "halo" refers to fluorine, chlorine, bromine and iodine.

The term "alkoxy" refers to alkyl—O—.

The term "alkanoyl" refers to alkyl—C(O)—.

The term "alkanoyloxy" refers to alkyl—C(O)—O—.

The terms "alkylamino" and "dialkylamino" refer to (alkyl)NH— and (alkyl)$_2$N—, respectively.

The term "alkanoylamino" refers to alkyl—C(O)—NH—.

The term "alkylthio" refers to alkyl—S—.

The term "alkylthiono" refers to alkyl—S(O)—.

The term "alkylsulfonyl" refers to alkyl—S(O)$_2$—.

The term "carbamyl" refers to —C(O)NH$_2$.

The term "alkoxycarbonyl" refers to alkyl—O—C(O)—.

The term "aryl" refers to phenyl, naphthyl, biphenyl and diphenyl groups, each of which may be substituted.

The term "aralkyl" refers to an aryl group bonded directly through an alkyl group, e.g., benzyl.

The term "substituted phenyl" refers to a phenyl group substituted by, for example, one to four substituents such as alkyl, halo, hydroxy, alkoxy, alkanoyl, alkanoyloxy, amino, alkylamino, dialkylamino, alkanoylamino, thiol, alkylthio, nitro, cyano, carboxy, carbamyl, alkoxycarbonyl, alkylthiono, alkylsulfonyl, sulfonamido and the like.

The compounds of formula I form salts which are also within the scope of this invention. Pharmaceutically acceptable (i.e., non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts may be obtained by exchanging, for example, the carboxylic acid protons in compound I with the desired ion in a medium in which the salt precipitates or in an aqueous medium followed by evaporation.

When compound I comprises a basic moiety, such as amino or substituted amino, it may form salts with a variety of organic and inorganic acids. Such salts include those formed with hydrogen chloride, hydrogen bromide, methanesulfonic acid, sulfuric acid, acetic acid, trifluoroacetic acid, maleic acid, benzenesulfonic acid, toluenesulfonic acid and various others (e.g., nitrates, phosphates, borates, tartrates, citrates, succinates, benzoates, ascorbates, salicylates and the like). Such salts may be formed by reacting compound I in an equivalent amount of the acid in a medium in which the salt precipitates or in an aqueous medium followed by evaporation.

In addition, zwitterions ("inner salts") may be formed.

It should be understood that the present invention is meant to include prodrug forms of the compounds of the formula I. While prodrug forms of the compounds of formula I are generally already represented herein (e.g., where Y is —CO$_2$R$^2$ and R$^2$ is alkyl), it is understood that any moiety at the Y position that will be cleaved in vivo to provide an acidic moiety is within the scope and spirit of the invention.

For example, compound I may be in the form of a prodrug having the formula

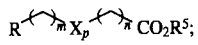 IIa

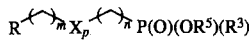 IIb wherein R$^5$ is:

lower alkyl, such as methyl, ethyl and the like;

substituted lower alkyl, such as 2-(N-morpholine)ethyl and the like;

lower aralkyl, such as benzyl, biphenylmethyl and the like;

(acyloxy)alkyl, such as (pivalyloxy)methyl, 1-(propanoyloxy)- 2-methyl-1-propyl and the like;

(aminoacyloxy)aroyloxyalkyl, such as paraglycyloxybenzoyloxymethyl and the like;

(aminoalkoxy)aroyloxyalkyl, such as para-2-[ (N-morpholine)ethoxy]benzoyloxymethyl and the like;

substituted amides, such as N,N-di(2-hydroxyethyl)acetamido, 4-methylpiperazine-1acetyl, 4-(2-hydroxyethyl)piperazine-1-acetyl and the like; or a dioxolanemethyl, such as (5-methyl-2-oxo- 1,3-dioxolan-4-yl)methyl and the like.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 42, p. 309–396, edited by K. Widder, et al. (Academic Press, 1985);

b) *A Textbook of Design and Development*, edited by Krogsgaard-Larsen and H. Bundgaard, Chapter 5, "Design and Application of Prodrugs", by H. Bundgaard, p. 113–191 (1991);

c) H. Bundgaard, *Advanced Drug Delivery Reviews*, 8, 1–38 (1992);

d) H. Bundgaard, et al., *Journal of Pharmaceutical Sciences*, 77, 285 (1988); and e) N. Kakeya, et al., *Chem Pharm Bull*, 32, 692 (1984).

It should further be understood that solvates (e.g., hydrates) of the compounds of formula I are also within the scope of the present invention. Methods of solvation are generally known in the art. Similarly, enantiomers and diastereomers of the compounds of formula I are within the scope of the present invention.

Preferred Moieties

For compounds of the formula I, the following moieties are preferred:

X is —ONR$^1$C(O)—, —NR$^1$C(O)— or N(OR$^1$)C(O)— when p is 1;

Y is —CO$_2$R$^2$ or —P(O) (OR$^2$) (R$^3$);

R is alkenylene;

R$^1$, R$^2$ and R$^4$ are each hydrogen or lower alkyl; and n is 1 or 2.

The following moieties are particularly preferred:

X is —ONHC(O)—, —NHC(O)— or —NOHC(O)— when p is 1;

Y is —CO$_2$H, —P(O) (OH) (OH) or —P(O) (OH) (CH$_3$);

R is alkenylene; and n is 1 or 2.

In particular, R is alkenylene of 8 to 15 carbons atoms.

Use and Utility

The compounds of formula I are inhibitors of S-farnesyl protein transferase. They are thus useful in the treatment of a variety of cancers, including (but not limited to) the following:

carcinoma, including that of the bladder, breast, colon, kidney, liver, lung, ovary, pancreas, stomach, cervix, thyroid and skin;

hematopoietic tumors of lymphoid lineage, including acute lymphocytic leukemia, B-cell lymphoma and Burketts lymphoma;

hematopoietic tumors of myeloid lineage, including acute and chronic myelogenous leukemias and promyelocytic leukemia;

tumors of mesenchymal origin, including fibrosarcoma and rhabdomyosarcoma; and other tumors, including melanoma, seminoma, tetratocarcinoma, neuroblastoma and glioma.

The compounds of formula I are especially useful in treatment of tumors having a high incidence of Ras involvement, such as colon, lung, and pancreatic tumors. By the administration of a composition having one (or a combination) of the compounds of this invention, development of tumors in a mammalian host is reduced.

Compounds of formula I may also be useful in the treatment of diseases other than cancer that may be associated with signal transduction pathways operating through Ras, e.g., neuro-fibromatosis.

Compounds of formula I may also be useful in the treatment of diseases associated with CAAX-containing proteins other than Ras (e.g., nuclear lamins and transducin) that are also post-translationally modified by the enzyme farnesyl protein transferase.

Compounds of formula I may also act as inhibitors of other prenyl transferases (e.g., geranylgeranyl transferase), and thus be effective in the treatment of diseases associated with other prenyl modifications (e.g., geranylgeranylation) of proteins (e.g., the rap, rab, rac and rho gene products and the like). For example, they may find use as drugs against Hepatitis delta virus (HDV) infections, as suggested by the recent finding that geranylgeranylation of the large isoform of the delta antigen of HDV is a requirement for productive viral infection [J. S. Glenn, et al., *Science*, 256, 1331 (1992)].

The compounds of this invention may also be useful in combination with known anti-cancer and cytotoxic agents. If formulated as a fixed dose, such combination products employ the compounds of this invention within the dosage range described below and the other pharmaceutically active agent within its approved dosage range. Compounds of formula I may be used sequentially with known anticancer or cytotoxic agents when a combination formulation is inappropriate.

The compounds of formula I of the invention additionally inhibit cholesterol biosynthesis by inhibition of de novo squalene production. These compounds inhibit the squalene synthetase enzyme and, in addition, some of the compounds of formula I of the invention inhibit other enzymes in the pathway from isopentenyl diphosphate to squalene, that is, farnesyl diphosphate synthetase and isopentenyl diphosphatedimethylallyl diphosphate isomerase.

Thus, the compounds of the invention are useful in treating atherosclerosis to inhibit progression of disease and in treating hyperlipidemia to inhibit development of atherosclerosis. In addition, the compounds of the invention may increase plasma high density lipoprotein cholesterol levels.

The compounds of the invention may also be employed in combination with an antihyperlipoproteinemic agent such as probucol and/or with one or more serum cholesterol lowering agents such as Lopid (gemfibrozil), bile acid sequestrants such as cholestyramine, colestipol, polidexide (DEAE-Sephadex) as well as clofibrate, nicotinic acid and its derivatives, neomycin, p-aminosalicyclic acid, bezafibrate and the like and/or one or more HMG CoA reductase inhibitors such as lovastatin, pravastatin, velostatin or simvastatin.

The compounds of this invention may be formulated with a pharmaceutical vehicle or diluent for oral, intravenous or subcutaneous administration. The pharmaceutical composition can be formulated in a classical manner using solid or liquid vehicles, diluents and additives appropriate to the desired mode of administration. Orally, the compounds can be administered in the form of tablets, capsules, granules, powders and the like. These compounds may be administered in a dosage range of about 0.05 to 50 mg/kg/day, preferably less than 50 mg/kg/day, in a single dose or in 2 to 4 divided doses. The compounds of the invention may also be employed with sodium lauryl sulfate or other pharmaceutically acceptable detergents to enhance oral bioavailability of such compounds.

Inhibition of squalene synthetase may be measured by the following procedure.

Rat liver microsomal squalene synthetase activity is measured using farnesyl diphosphate as substrate and quantitating squalene synthesis using gas chromatographic analysis. The assay was developed by modifying conditions originally described by Agnew (Methods in Enzymology 110:357, 1985). Alternatively, squalene synthetase activity can be measured by the procedure of C. P. Ciosek et al., *J. Biol, Chem,*, 268, 24832–24837, 1993.

Process of Preparation

Scheme I

Alkylation of a compound of the formula III wherein L is a suitable leaving group (e.g., halide, rosylate, mesylate, triflate and the like):

  III with a hydroxyl amine of the formula IV:

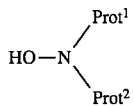

wherein Prot¹ and Prot² are suitable nitrogen protecting groups (e.g., phthaloyl and the like), provides a compound of the formula V:

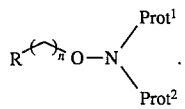  V

A compound of the formula V can also be prepared by a Mitsunobu reaction with a compound of the formula IV, where Prot¹ and Prot² combine to form a phthalimido group, and a suitable alcohol, using standard reagents like diethylazodicarboxylate (DEAD) and triphenylphosphine.

Removal of the nitrogen protecting group in an appropriate manner, e.g., by treatment with hydrazine or N-methylhydrazine when Prot¹ and Prot² are phthalimido, gives the alkoxyamine of the formula VI:

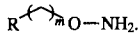 VI

Treatment of an alkoxyamine of the formula VI with a compound of the formula VII:

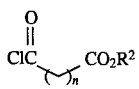 VII provides a compound of the formula VIII:

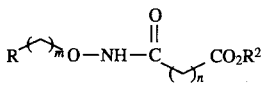 VIII which can be de-esterified.

Similarly, alkylation of the alkoxyamine of the formula VI with an alkylating agent of the formula VIIa:

VIIa R²—L wherein L is a suitable leaving group, provides the N-alkylated alkoxyamine VIIIa:

 VIIIa

The Michaelis-Becker type reaction of a phosphonite monoester or a phosphite diester ($R^1$ is $OR^5$) of the formula IX:

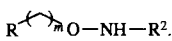 IX with an ester halide of the the formula X, where L is a suitable leaving group:

$$R^6O\underset{O}{\overset{}{\|}}\overset{}{C}\text{—}(\,)_n\text{—}L \quad X$$

provides the phosphinyl-carboxyl mixed esters of the general formula XI:

$$R^6O\underset{O}{\overset{}{\|}}\overset{}{C}\text{—}(\,)_n\text{—}\underset{O}{\overset{OR^5}{\underset{\|}{P}}}\text{—}R^1. \quad XI$$

A compound of the formula XI, where m is 2, may also be alternatively prepared by Michael type addition of a compound of the formula IX to an acrylate ester of the formula XII:

$$R^6O\underset{O}{\overset{}{\|}}\overset{}{C}\text{—}CH\text{=}CH_2. \quad XII$$

Selective hydrolysis of the carboxyl ester of the formula XI then provides the carboxylic acid of the formula XIII:

$$HO\underset{O}{\overset{}{\|}}\overset{}{C}\text{—}(\,)_n\text{—}\underset{O}{\overset{OR^5}{\underset{\|}{P}}}\text{—}R^1. \quad XIII$$

This type of selective hydrolysis can be performed by treatment of a compound of the formula XI with one equivalent of an alkali metal base in an organic or mixed aqueous/organic solvent. Suitable alkali metal bases are lithium, sodium or potassium hydroxide, carbonate or bicarbonate. Suitable organic solvents are methanol, ethanol, isopropanol, tetrahydofuran, dioxane and the like. Alternatively, when $R^6$ is benzyl and $R^5$ is methyl or ethyl, the $R^6$ protecting group of a compound of the formula XI can be selectively removed by hydrogen in the presence of a catalyst (e.g., palladium hydroxide or palladium on carbon) to provide a compound of the formula XIII.

Coupling of an amine of the formula VI with an acid of the formula XIII provides the hydroxamic ether of the formula XIV:

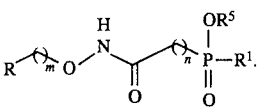 XIV

A variety of coupling reagents may be used for this coupling, including 1-(3-dimethylaminopropyl)-3-ethylcarbodiimide hydrochloride (EDC) with 1-hydroxybenzotriazole (HOBt), dicyclohexylcarbodiimide (DCC) with HOBt, benzotriazol-1-yloxytris(dimethylamino)phosphonium hexafluorophosphate (BOP) with or without HOBt, carbonyldiimidazole (CDI), DCC and pentafluorophenol, bis(2-oxo- 3-oxazolidinyl)phosphinic chloride (BOP chloride); isopropylchtoroformate (IPCF); and the like. The acid chloride derivative of the formula XIII may also be directly used in the presence of an alkali metal (e.g., potassium carbonate) or an organic base (e.g., diisopropylethylamine) in an organic solvent (e.g., dimethylformamide (DMF), tetrahydrofuran (THF), dichloromethane, and the like) in this coupling reaction to provide a compound of the formula XIV.

Alkylation of the hydroxamic ether of the formula XIV with an alkylating agent of the formula VII, using an alkali metal or organic base, provides the N-alkylated compound of the formula XV:

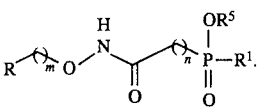 XV

Alternatively, a compound of the formula XV may also be prepared by coupling an N-alkylated alkoxyamine of the formula VIII with an acid of the formula XIII.

Scheme II

Coupling of an amine of the formula XVI:

$$R\text{—}(\,)_m\text{—}NHR^3 \quad XVI$$

with an acid of the formula XIII provides the amide of the formula XVII:

$$R\text{—}(\,)_m\text{—}\underset{}{\overset{R^3}{\underset{|}{N}}}\text{—}\underset{O}{\overset{}{\|}}\overset{}{C}\text{—}(\,)_n\text{—}\underset{O}{\overset{OR^5}{\underset{\|}{P}}}\text{—}R^1. \quad XVII$$

Treating an amine of the formula XVI with a compound of the formula VII provides a compound of the formula XVIIa:

$$R\text{—}(\,)_m\text{—}NH\text{—}\underset{O}{\overset{}{\|}}\overset{}{C}\text{—}(\,)_n\text{—}CO_2R^2 \quad XVIIa$$

which can be de-esterified.

Scheme III

Alkylation of an O-protected alkoxyamine of the formula XVIII, where Prot³ is a suitable protecting group (benzyl, 2-tetrahydropyranyl (THP), etc.):

XVIII H₂N—OProt³ with the alkylating agent of the formula III, in the presence of an alkali metal or organic base, provides the alkoxyamine of formula XIX:

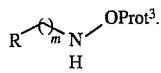    XIX

Treatment of a compound of the formula XIX with a compound of the formula VII provides a compound of the formula XX:

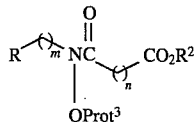    XX which can be deprotected and de-esterified.

Coupling a compound of the formula XIX with an acid of the formula XIII under regular conditions provides a compound of the formula XXa:

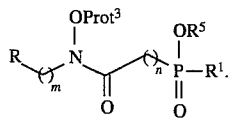    XXa

When Prot³ is THP, a compound of the formula XX may be treated with a mild acid (e.g., p-toluene sulfonic acid (TsOH)) in an organic solvent (methanol, tetrahydrofuran (THF), etc.) to form a compound of the formula XXI. When Prot³ is benzyl and the R and R¹ groups do not contain a triple bond or a non-aromatic double bond, the compound of the formula XXa may be converted to a compound of the formula XXI under conventional hydrogenation conditions (e.g., hydrogenation in methanol in the presence of a catalyst like palladium/carbon):

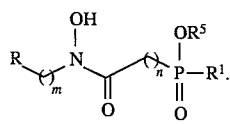    XXI

For intermediates of the formulas XIV, XV, XVII and XXI, the phosphorous protecting group(s) can be removed by methods known in the art. For example, when R¹ is OR⁵, the phosphonate diesters can be converted to the corresponding phosphonic diacids by treatment with bromotrimethylsilane (TMSBr) in dichloromethane in the presence of an acid scavenger like bis(trimethylsilyl)trifluoroacetamide (BSTFA). When R¹ is not OR⁵, the phosphinate monoester can be converted to the phosphinic acid by treatment with TMSBr/BSTFA, or also by basic hydrolysis (e.g., NaOH/CH₃OH). When R⁵ is methyl, the deprotection can also be carried out by nucleophilic dealkylation using reagents like sodium iodide (NaI) or trimethylamine ((CH₃)₃N).

Using appropriate methods as outlined above, deprotection of a compound of the formula XIV provides a compound of the formula I where

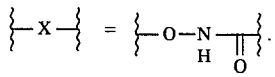

Deprotection of a compound of the formula XV provides a compound of the formula I where

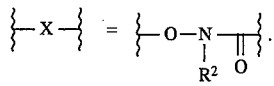

Deprotection of a compound of the formula XVII provides a compound of the formula I where

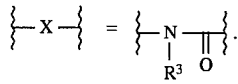

Deprotection of a compound of the formula XXI provides a compound of the formula I where

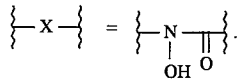

Prodrugs of the compounds of general formula I may be prepared by methods known in the art. For example, a compound of the formula I, where R³ is lower alkyl, may be treated with a double ester type prodrug forming derivative of the formula XXII (where R⁷ is hydrogen or lower alkyl, and R⁸ is lower alkyl):

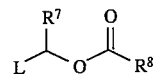

to provide a compound of the formula XXIII. Compound XXIII is a prodrug when R³ is OH or lower alkyl:

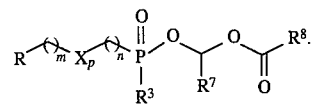    XXIII

Such alkylations can be performed by methods known in the art. When R³ is OH, alkylation should be performed under controlled conditions with limited amounts of the compound of the formula XXII to avoid dialkylation.

Alternatively, a prodrug where R³ is OH may also be prepared by reacting a compound of the formula XXII with a specific compound of the formula XIV:

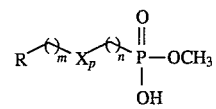    XIVa to provide an intermediate of the formula XXV:

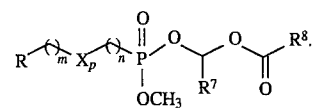    XXV

Selective dealkylation of the compound of the formula XXV with trimethylamine or tetraalkylammonium halide provides the prodrug II where R³ is OCH₃.

Protecting groups may be used in these processes with substituents having reactive functionalities, such as hydroxyl, carboxyl, amino, mercapto, guanidino, imidazolyl, indolyl and the like. The particular protecting groups used depend upon the reactive functionality to be protected and are generally known in the art. Exemplary sidechain protecting groups include acetyl, benzoyl, benzyl, t-butyl and the like for hydroxyl; cyclohexyl, benzyl, methyl, ethyl, t-butyl and the like for carboxyl; benzyl, 4-methylbenzyl, 4-methoxybenzyl, acetyl, acetamidomethyl, triphenylmethyl (trityl) and the like for mercapto; t-butoxycarbonyl (Boc), benzyloxylcarbonyl (Cbz), N-[(9H-Fluoren-9-ylmethoxy)carbonyl] (Fmoc), phthaloyl (Pht), p-toluenesulfonyl (Tos), trifluoroacetyl, 2-(trimethylsilyl)ethoxycarbonyl (Teoc) and the like for amino; 2,4-dinitrophenyl, benzyloxymethyl, Tos, Boc, trityl and the like for imidazolyl; formyl, Cbz, Teoc, 2,2,2-trichloroethyl carbamate (TROC) and the like for indolyl; and tosyl, nitro, bis(1-adamantyloxycarbonyl) and the like for guanidino.

Protecting groups may be removed, if desired, by, for example, treatment with one or more deprotecting agents in an inert solvent or solvent mixture. For examples of protecting groups and suitable deprotecting agents, see M. Bodansky and A. Bodansky, "The Practice of Peptide Synthesis", Springer-Verlag, Inc. (1984); and T. W. Greene and P. G. M. Wuts, "Protective Groups in Organic Synthesis", Second Edition, John Wiley & Sons, New York, 1991.

The invention will now be further described by the following working examples, which are preferred embodiments of the invention. All temperatures are in degrees Celsius (°C.) unless otherwise indicated. Compounds exemplified herein, which comprise a basic moiety such as an amine or substituted amine, may exist as a salt of an organic or inorganic acid. This information is not necessarily explicitly described in all the examples, but would be understood by those skilled in the art. These examples are illustrative rather than limiting.

EXAMPLE 1

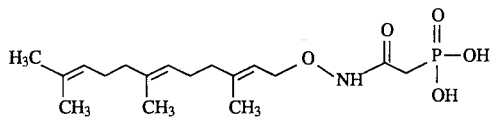

(E,E)-[2-Oxo-2-[[(3,7,11-trimethyl-2,6,10-dodecatrienyl)oxy] amino]ethyl]phosphonic acid, disodium salt A. ((3,7,11-trimethyl-2,6,10-dodecatrienyl) oxy)amine, hydrochloride Potassium carbonate (25.3 g, 182 mmol) was added to a solution of hydroxyphthalimide (11.4 g, 70.1 mmol) in dimethylformamide (DMF) (150 ml), and the solution was stirred for 15 minutes at 0° C. Farnesyl bromide (18.9 ml, 70.1 mmol) was added portionwise, and the mixture was warmed to room temperature and stirred for 3 hours. The reaction was quenched with 10% lithium chloride (LiCl) (150 ml) and extracted with ethyl acetate (4×200 ml). The combined organic extracts were washed with 10% LiCl (3×200 ml), dried with magnesium sulfate ($MgSO_4$), filtered and concentrated under vacuum. The residue was recrystallized from hexane to afford the phthalimide derivative of compound A, mp: 53°–55° C. Methylhydrazine (15.7 ml, 296 mmol) was added to a solution of this compound (21.0 g, 59.1 mmol) in ethanol (150 ml), the solution was stirred for 2 hours, sodium hydroxide (1N, 75 ml) was added and the solution was stirred for 15 minutes. The reaction was concentrated under vacuum, dissolved in potassium hydroxide (KOH) (1N, 300 ml) and extracted with ethyl acetate (4×100 ml). The combined organic extracts were washed with KOH (1N, 2×150 ml), dried ($MgSO_4$), filtered and concentrated under vacuum. The residue was dissolved in diethylether (100 ml) and cooled to 0° C., and anhydrous hydrochloric acid (HCl) (4M, 22.2 ml) in dioxane was added with swirling. The solid was filtered and the filtered material washed with petroleum ether at −78° C. The solid was dried under vacuum to afford compound A (14.8 g, 91%), mp: 101°–106° C.

B. (E,E)-[2-Oxo-2-[[(3,7,11-trimethyl- 2,6,10-dodecatrienyl)oxy]amino]ethyl] phosphonic acid, dimethyl ester Diisopropylethylamine (11.5 ml, 65.8 mmol) was added to a solution of O,O-dimethylphosphonoacetate (3.7 g, 21.9 mmol) and compound A (6.0, 21.9 mmol) in acetonitrile (48 ml) and DMF (16 ml). To the mixture was added benzotriazol-1-yloxytris(dimethylamino)phosphonium hexafluorophosphate (BOP) (10.7 g, 24.1 mmol) and the reaction was stirred an additional 16 hours. The reaction was quenched with 1N HCl (75 ml) and extracted with ethyl acetate (4×50 ml). The combined organic extracts were washed with 10% sodium bicarbonate ($NaHCO_3$) (75 ml) and 10% LiCl (3 ×70 ml), dried ($MgSO_4$), filtered and concentrated under vacuum. The residue was purified by flash chromatography (1:1 acetone/hexane) to afford compound B (8.5 g, 100%).

TLC: $R_f$=0.58 (1:1 acetone/hexane, visualization by PMA)

C. (E,E)-[2-Oxo-2-[[(3,7,11-trimethyl- 2,6,10-dodecatrienyl)oxy]amino]ethyl]phosphonic acid, disodium salt Sodium hydroxide (1N, 65.1 ml, 65.1 mmol) was added to a solution of compound B (8.4 g, 21.7 mmol) in methanol (70 ml) and the solution was stirred at reflux for 16 hours. The reaction was concentrated under vacuum, dissolved in HCl (1N, 50 ml) and extracted with dichloromethane (4×50 ml). The combined organic extracts were dried ($MgSO_4$), filtered and concentrated under vacuum. The residue was dissolved in ethyl acetate (75 ml) and extracted with sodium hydroxide (NaOH) (1N, 1×22 ml). The organic layer was discarded and the aqueous layer was lyophilized to afford 4.35 g (51%) of the monomethyl ester, monosodium salt of the title compound, mp: 87°–93° C. HCl (1N, 50 ml) was added to a portion of this material (1.3 g, 3.3 mmol) and the solution was extracted with dichloromethane (4×50 ml). The combined organic extracts were dried ($MgSO_4$), filtered and concentrated under vacuum to afford the monoacid (1.2 g, 3.22 mmol). Bis(trimethylsilyl)trifluoroacetamide (3.42 ml, 12.9 mmol) was added to a solution of this material (1.2 g, 3.22 mmol) in dichloromethane (20 ml) and the solution was stirred for 1 hour. Bromotrimethylsilane (0.51 ml, 3.86 mmol) was added and the mixture was stirred for 4 hours. The reaction was concentrated under vacuum and the residue dissolved in methanol (10 ml). The solution was stirred for 15 minutes and concentrated under vacuum. The residue was dissolved in methanol (10 ml), and 40% aqueous tetrabutyl ammonium hydroxide (20 ml) was added. The solution was lyophilized and the residue was purified by CHP-20P gel (eluting sequentially with water (500 ml) and 80% aqueous methanol (200 ml)) followed by concentration of appropriate fractions under vacuum to afford the ammonium salt of the title compound. A portion of this material (0.606 g, 0.72 mmol) was dissolved in water (1.0 ml) and the solution was passed through a Dowex $Na^+$ ion exchange column (eluting with water). The appropriate fractions were concentrated, millipore filtered and lyophilized to afford the title compound (0.06 g, 21%), mp: decomposition above 210° C.

Analysis for $C_{17}H_{28}NO_5PNa_2 \cdot 0.91\ H_2O$

Calculated: C, 48.63; H, 7.16; N, 3.34.

Found: C, 48.39; H, 7.26; N, 3.58.

EXAMPLE 2

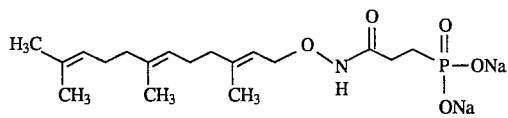

(E,E)-[3-[[(3,7,11-Trimethyl-2,6,10-dodecatrienyl)oxy]
amino]-3-oxypropyl]-phosphonic acid, disodium salt A. (E,E)-[3-[[(3,7,11-Trimethyl-2,6,10-dodecatrienyl)oxy] amino]-3-oxypropyl]-phosphonic acid, dimethyl ester 1,1'-Carbonyldiimidazole (0.32 g, 2.0 mmol) was added to a solution of compound B of Example 8 (0.36 g, 2.0 mmol, the preparation of which is described therein) in tetrahydrofuran (THF) (5 ml), and the resultant mixture was stirred for 15 minutes at 0° C. and 1 hour at 20° C. Compound A of Example 1 (0.54 g, 2.0 mmol) was added, followed by diisopropylethylamine (0.70 ml, 4.0 mmol), and the mixture was stirred for 16 hours at room temperature. The reaction was quenched with $NaHCO_3$ (saturated, 50 ml) and extracted with ethyl acetate (3×50 ml), and the combined organic extracts were dried ($MgSO_4$), filtered and concentrated under vacuum. The residue was purified by flash chromatography (2:1 hexane/acetone) to afford compound A (0.58 g, 72%).

TLC: $R_f$=0.26 (1:1 hexane/acetone, visualization by PMA)

B. (E,E)-[3-[[(3,7,11-Trimethyl-2,6,10-dodecatrienyl)oxy] amino]-3-oxypropyl]-phosphonic acid, disodium salt Bis (trimethylsilyl) trifluoroacetamide (0.60 ml, 2.2 mmol) was added to a solution of compound A (0.2 g, 0.49 mmol) in dichloromethane (4 ml) and the mixture was stirred for 1 hour. Bromotrimethylsilane (0.16 ml, 1.2 mmol) was added and the mixture was stirred for 16 hours and concentrated under vacuum. The residue was dissolved in methanol (5 ml) and NaOH (1N, 1.1 ml) and the mixture was stirred for 15 minutes and concentrated under vacuum. The residue was purified by SP-207 gel (eluting sequentially with water (250 ml) and methanol (30%, 500 ml)) to afford the title compound, mp: 203°–212° C. with decomposition.

Analysis for $C_{18}H_{30}NO_5PNa_2$–1.25 $H_2O$
Calculated: C, 49.14; H, 7.45; N, 3.18.
Found: C, 49.09; H, 7.89; N, 3.37.

EXAMPLE 3

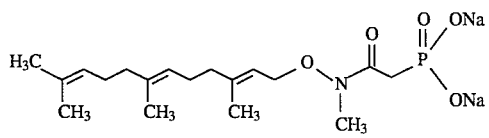

(E,E)-[2-Methyl-[(3,7,11-trimethyl-2,6,10-dodecatrienyl)oxy] amino]-2-oxoethyl]-phosphonic acid, disodium salt A. (E,E)-[2-Oxo-2-[[(3,7,11-trimethyl-2,6,10-dodecatrienyl)oxy)amino)ethyl]-phosphonic acid, diethyl ester Compound A was prepared from compound A of Example 1 and O,O-diethylphosphonoacetate as described for compound A of Example 2.

TLC: $R_f$=0.61 (1:1 hexane/acetone, visualization by PMA)

B. (E,E)-[2-Methyl-[(3,7,11-trimethyl- 2,6,10-dodecatrienyl)oxy]amino]-2-oxoethyl]-phosphonic acid, diethyl ester Potassium carbonate (0.34 g, 2.4 retool) was added to a solution of compound A (0.34 g, 0.82 mmol) in acetone (5 ml) and the mixture was stirred for 5 minutes. Methyl iodide (0.25 ml, 4.1 mmol) was added to the mixture and it was stirred for 16 hours. The reaction was filtered, the filtrate was concentrated under vacuum and the residue was purified by flash chromatography (eluting with 3:1 hexane/acetone) to afford compound B (0.21 g, 87%).

TLC: $R_f$=0.63 (1: 1 hexane/acetone, visualization by PMA)

C. (E,E)-[2-Methyl-[(3,7,11-trimethyl- 2,6,10-dodecatrienyl)oxy]amino]-2-oxoethyl]-phosphonic acid, disodium salt The title compound was prepared from compound B as described for Example 2.

mp: decomposition above 180° C.
Analysis for $C_{18}H_{30}O_5NPNa_2$–0.14 $H_2O$
Calculated: C, 51.49; H, 7.27; N, 3.34.
Found: C, 51.28; H, 7.70; N, 3.55.

EXAMPLE 4

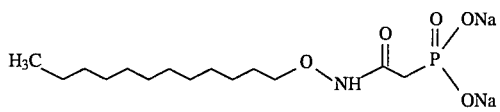

[2-[(Dodecyloxy)amino]-2-oxoethyl]phosphonic acid, disodium salt

A. 1-(Dodecyloxy)-amine, hydrochloride

Compound A was prepared from 1-bromododecane and N-hydroxypthalimide followed by treatment with methylhydrazine and then hydrogen chloride as described for compound A of Example 1.

mp: 135°–140° C.

B. [2-[(Dodecyloxy)amino]-2-oxoethyl]-phosphonic acid, diethyl ester

Compound B was prepared from compound A and (O,O-diethylphosphono)-acetic acid as described for compound A from Example 2.

MS: $(M+H)^+$ 380

C. [2-[(Dodecyloxy)amino]-2-oxoethyl]-phosphonic acid, disodium salt

The title compound was prepared from compound B as described for Example 2. Chromatography on CHP-20P gel (eluting sequentially with water and 70% aqueous methanol) afforded the title compound, mp: decomposition above 170° C.

Analysis for $C_{14}H_{28}NO_5PNa_2$–0.55 $H_2O$
Calculated: C, 44.57; H, 7.78; N, 3.71.
Found: C, 44.71; H, 8.17; N, 3.57.

EXAMPLE 5

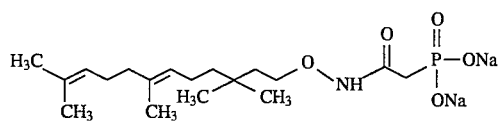

(E)-[2-[[(3,3,7,11-Tetramethyl-6,10-dodecadienyl)oxy)-amino]- 2-oxoethyl]-phosphonic acid, disodium salt A. 3,7,11-Trimethyl-2,6,10-dodecatrien-1-al A solution of dimethylsulfoxide (7.9 ml, 83 mmol) in dichloromethane (30 ml) was added to a solution of oxalyl chloride (4.7 ml, 54 mmol) in dichloromethane (120 ml) at –65° C. and the solution was stirred 10 minutes with a mechanical stirrer. A solution of famesol (10 gm, 45 mmol) in dichloromethane (30 ml) was added dropwise over 20 minutes maintaining a temperature of –63° C., and the solution was stirred an additional 30 minutes at –65° C. Trimethylamine (38 ml, 270 mmol) was added dropwise over 20 minutes and the solution was stirred an additional 15 minutes at –65° C. After warming to room temperature, the reaction was quenched with water (500 ml) and extracted with dichloromethane (2×200 ml). The combined organic extracts were washed sequentially with with HCl (1N, 4×100 ml) and sodium carbonate (Na$_2$CO$_3$) (1× 100 ml), dried (MgSO$_4$), filtered and concentrated under vacuum to afford compound A.

MS: (M+H)$^+$ 221

B. 3,3,7,11-Tetramethyl-6,10-dodecadien-1-al

Methyl lithium (1.4M, 145 mmol) was added dropwise while maintaining a temperature below −50° C. to a mechanically stirred solution of CuI (14.6 g, 76.4 mmol) in THF (200 ml). The reaction was stirred at −78° C. for 15 minutes, 0° C. for 15 minutes and room temperature for 5 minutes, and recooled to −78° C. Tetramethylethylenediamine (27.5 ml, 182 mmol) was added dropwise, keeping the temperature below −60° C., and the solution was stirred at −78° C. for 45 minutes. Trimethylsilylchloride (23.1 ml, 182 mmol) was added dropwise and the solution was stirred for 30 minutes at −78° C. A solution of compound A (8 g, 36 mmol) in THF (30 ml) was added dropwise and the solution was stirred for 3.5 hours at −78° C. The reaction was quenched at −78° C. with HCl (1N, 500 ml), warmed to room temperature and extracted with diethyl ether (4× 150 ml). The combined organic extracts were washed with potassium hydroxide (KOH) (1N, 300 ml), dried (MgSO$_4$), filtered and concentrated under vacuum. The residue was purified by flash chromatography (silica gel, 100–200 mesh, eluting with 9:1 petroleum ether/diethyl ether) to afford compound B (5.7 g, 66%).

MS: (M+H)$^+$ 237

C. 3,3,7,11-Tetramethyl-6,10-dodecadien-1-ol

Sodium borohydride (0.63 g, 17 mmol) was added to a solution of compound B (2.8 g, 12 mmol) in methanol (50 ml) at 0° C., and the solution was stirred 0.5 hours. The reaction was quenched with saturated ammonium chloride (2 ml) and concentrated under vacuum. The residue was diluted with saturated ammonium chloride (50 ml) and extracted with diethyl ether (4×50 ml), and the combined organic extracts were dried (MgSO$_4$), filtered and concentrated under vacuum. The residue was purified by flash chromatography (3:1 petroleum ether/diethyl ether) to afford compound C.

MS: (M+H)$^+$ 239

D. N-(1-(3,3,7,11-Tetramethyl-6,10-dodecadienyl)oxy)-phthalimide

A solution of compound C (2.75 g, 11.5 mmol) in THF (10 ml) was added to a solution of N-hydroxyphthalimide (3.77 g, 23.1 mmol) and triphenylphosphine (7.6 g, 28.9 mmol) in THF (25 ml). The mixture was cooled to −78° C. and diethylazodicarboxylate (3.6 ml, 23.1 mmol) was added dropwise. After 20 minutes at −78° C., the reaction was warmed to room temperature and stirred for 2 hours. The reaction was concentrated under vacuum and the residue purified by flash chromatography (10:1 hexane/ethyl acetate) to afford 4.23 g (96%) of compound D.

MS: (M+H)$^+$ 384

E. (1-(3,3,7,11-Tetramethyl-6,10-dodecadienyl)oxy)amine

Compound E was prepared from compound D as described for the hydrazinolysis in the preparation of compound A of Example 1. Following extraction, Compound E was purified by flash chromatography (4:1 hexane/ethyl acetate) to afford compound E.

MS: (M+H)$^+$ 254

F. (E)-[2-[[(3,3,7,11-Tetramethyl-6,10-dodecadienyl)oxy)-amino]- 2-oxoethyl]-phosphonic acid, diethyl ester Compound F was prepared from compound E and (O,O-diethylphosphono)-acetic acid as described for compound A from Example 2.

MS: (M+H)$^+$ 432

G. (E)-[2-[[(3,3,7,11-Tetramethyl-6,10-dodecadienyl)oxy)-amino]- 2-oxoethyl]-phosphonic acid, disodium salt The title compound was prepared from compound F as described for Example 2. Chromatography on CHP-20P gel (eluting sequentially with water and 70% aqueous methanol) afforded the title compound, mp: decomposition above 205° C.

Analysis for C$_{18}$H$_{32}$NO$_5$PNa$_2$–0.5 H$_2$O
Calculated: C, 50.47; H, 7.76; N, 3.27.
Found: C, 50.43; H, 8.16; N, 3.16.

EXAMPLE 6

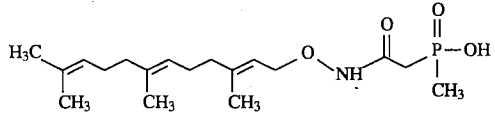

(E,E)-Methyl-[2-oxo-2-[[(3,7,11-trimethyl-2,6,10-dodecatrienyl)oxy] amino]ethyl]-phosphinic acid, monosodium salt A. (E,E)-Methyl-[2-oxo-2-[[(3,7,11- trimethyl- 2,6,10-dodecatrienyl)oxy]amino]ethyl]-phosphinic acid, ethyl ester Compound A was prepared from compound A of Example 1 and (O-ethyl-methylphosphinyl)-acetate as described for compound B of Example 1.

MS: (M+H)$^+$ 386

B. (E,E)-Methyl-[2-oxo-2-[[(3,7,11-trimethyl- 2,6,10-dodecatrienyl)oxy]amino]ethyl]-phosphinic acid, monosodium salt The title compound was prepared from compound A as described for Example 2. Chromatography on CHP-20P gel (eluting sequentially with water and 30% aqueous methanol) afforded the title compound, mp: 125°–135° C.

Analysis for C$_{18}$H$_{31}$NO$_4$PNa
Calculated: C, 56.98; H, 8.24; N, 3.69.
Found: C, 56.83; H, 8.63; N, 3.44.

EXAMPLE 7

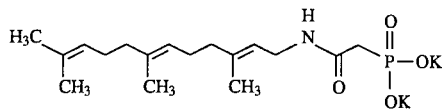

(E,E)-[2-Oxo-2-[[(3,7,11-trimethyl-2,6,10-dodecatrienyl)-amino] ethyl]phosphonic acid, dipotassium salt A. (E,E)-[2-Oxo-2-[[(3,7,11-trimethyl- 2,6,10-dodecatrienyl)amino]ethyl]-phosphonic acid, diethyl ester A solution of 562 mg (2.87 mmol) of (O,O-diethylphosphono)-acetic acid in 7.0 mL of THF at 0° C. under argon was treated with 465 mg (287 mmol) of 1,1'-carbonyldiimidazole and the resultant mixture was stirred for 15 minutes at 0° C. and one hour at room temperature. A solution of 700 mg (3.16 mmol) of farnesyl amine in 5 mL of THF was added and the resulting mixture was stirred for six hours at room temperature. After diluting with 100 mL of ethyl ether, the organic phase was washed with 20 mL of 1M HCl, 20 mL of NaHCO$_3$, and 20 mL of brine, dried over MgSO$_4$ and evaporated to obtain 1.28 g of a colorless oil. Purification required two chromatographies. Column I was run on 120 g of silica and eluted with 92:8 ethyl acetate::petroleum ether, and provided 622.0 mg of pure compound A coeluting with an impurity. Column II was run on 25 g of silica. The impure fraction from Column I was eluted with 85:15 ethyl acetate:petroleum ether to obtain an additional 115.4 mg of pure compound A, for a combined yield of 737 mg (58%).

B. (E,E)-[2-Oxo-2-[[(3,7,11-trimethyl- 2,6,10-dodecatrienyl)amino]ethyl]-phosphonic acid, dipotassium salt A solution of 737 mg (1.85 mmol) of compound A and 490 μL (3.7 mmol) of collidine in 12 mL of dry dichloromethane was stirred for 1 hour at 0° C. and for 20 hours at room temperature. The solvent was evaporated. The residue was dissolved in a mixture of 1.03 mL (7.4 mmol) of triethylamine and 4 mL of methanol, stirred 15 minutes and evaporated. The organic phase formed on addition of 75 mL of ethyl acetate was washed with 15 mL of 10% HCl, 15 mL of 1:1 H$_2$O:brine, and 15 mL of brine, dried over MgSO$_4$ and evaporated. The resulting oil was dissolved in a mixture of 4.6 mL (4.6 mmol) of 1M KOH and 4 mL of methanol. After evaporating the methanol, the water was removed by lyophilization. The lyophilizate was dissolved in 4 mL of water and loaded onto a 2.5 cm diameter× 15 cm length column of HP-20, packed in water. Appropriate fractions were combined, lyophilzed and the resulting white powder was further dried at high vacuum over phosphorus pentoxide to provide 488 mg (63%) of the title compound.

$^{31}$P-NMR (CD$_3$OD) d 12.5 (singlet) ppm. (109 MHz, 85% H$_3$PO$_4$ or extended reference)

Anal. Calculated for C$_{17}$H$_{29}$KNO$_4$P (MW 381.502) C. 48.66; H, 6.73; N, 3.34; P, 7.38.

Found: C, 48.63; H, 7.15; N, 3.28; P, 7.0.

EXAMPLE 8

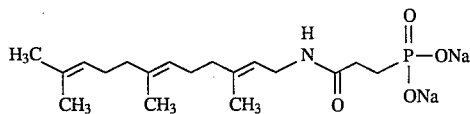

(E,E)-[3-Oxo-3-[(3,7,11-trimethyl-2,6,10-dodecatrienyl)-amino] propyl]phosphonic acid, disodium salt A. (O,O-Dimethylphosphono)-propionic acid, ethyl ester Dimethyl trimethylsilylphosphite (19.5 g, 0.107 mol) and ethyl acrylate (9.67 ml, 0.089 mol) were heated neat for 2 hours at 117° C. The reaction was cooled to room temperature, diluted with diethyl ether (200 ml) and slowly quenched with water (10 ml). The mixture was stirred for 15 minutes, dried (MgSO$_4$) and concentrated under vacuum. The residue was purified by vacuum distillation (115°–120° C., 1.5 mm Hg) to afford compound A (9.0 g, 40%).

MS: (M+H)$^+$ 211

B. (O,O-Dimethylphosphono)-propionic acid

Sodium hydroxide (1N, 4.76 ml) was added to a solution of compound A (1.0 g, 4.76 mmol) in methanol (5 ml) at 0° C. The solution was allowed to warm to room temperature and stirred for 16 hours. The reaction was concentrated under vacuum and the residue dissolved in water (10 ml) and extracted with dichloromethane (3×50 ml). The organic extracts were discarded, and the aqueous layer acidified to pH 2.0 (1N HCl) and concentrated under vacuum. The residue was dissolved in ethyl acetate (25 ml), dried (MgSO$_4$), filtered and concentrated under vacuum to afford compound B (0.78 g, 90%).

MS: (M+H)$^+$ 183

C. (E,E)-[3-Oxo-3-[(3,7,11-trimethyl- 2,6,10-dodecatrienyl)amino]propyl]-phosphonic acid, dimethyl ester Compound C was prepared from compound B and (3,7,11-trimethyl-2,6,10-dodecatrienyl)-amine, hydrochloride as described for compound A of Example 2. Chromatography on silica with 25:1 chloroform/methanol afforded compound C.

MS: (M+H)$^+$ 386

D. (E,E)-[3-Oxo-3-[(3,7,11-trimethyl- 2,6,10-dodecatrienyl)amino]propyl]-phosphonic acid, disodium salt The title compound was prepared from compound C as described for Example 2, with chromatography on CHP-20P gel eluting sequentially with water and acetonitrile.

mp: decomposition above 195° C.

Analysis for C$_{18}$H$_{30}$NO$_4$PNa$_2$–0.11 H$_2$O

Calculated: C, 53.61; H, 7.55; N, 3.47.

Found: C, 53.91; H, 8.00; N, 3.34.

EXAMPLE 9

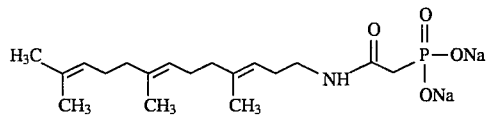

(E,E)-[2-Oxo-2-[(4,8,12-trimethyl-3,7,11-tridecatrienyl)-amino] ethyl]phosphonic acid, disodium salt A. (4,8,12-trimethyl-3,7,11-tridecatrienyl)-amine Aluminum chloride (0.369 g, 2.76 mmol) was added in one portion to a solution of lithium aluminum hydride (LiAlH$_4$) (1M, 2.76 ml, 2.76 mmol) in diethyl ether (10 ml) at 0° C. and stirred at room temperature for 15 minutes. A solution of 4,8,12-trimethyl-3,7,11-tridecatrienylnitrile (0.58 g, 2.5 mmol) in diethyl ether (10 ml) was added dropwise to the mixture and stirred for 2.5 hours at room temperature. The reaction was quenched with sodium carbonate (10%, 2 ml), diluted with water (50 ml) and extracted with diethyl ether (4× 50 ml). The combined organic extracts were dried (MgSO$_4$), filtered and concentrated under vacuum. The residue was dissolved in diethyl ether (20 ml), cooled to 0° C. and treated with anhydrous HCl in dioxane (4M, 1.2 ml). The resulting precipitate was filtered and dried under vacuum to afford compound A (0.48 g, 70%), mp: 81°–87° C.

B. (E,E)-[2-Oxo-2-[(4,8,12-trimethyl- 3,7,11-tridecatrienyl)amino]ethyl]-phosphonic acid, diethyl ester Compound B was prepared from compound A and (O,O-diethylphosphono)-acetic acid as described for compound A of Example 2.

MS: (M+H)$^+$ 414

C. (E,E)-[2-Oxo-2-[(4,8,12-trimethyl- 3,7,11-tridecatrienyl)amino]ethyl]-phosphonic acid, disodium salt The title compound was prepared from compound B as described for Example 2, with chromatography on CHP-20P gel, eluting sequentially with water and acetonitrile.

mp: decomposition above 185° C.

Analysis for C$_{18}$H$_{30}$NO$_4$PNa$_2$–0.38 H$_2$O

Calculated: C, 52.96; H, 7.59; N, 3.43.

Found: C, 52.94; H, 7.85; N, 3.45.

EXAMPLE 10

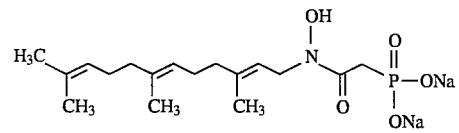

(E,E)-[2-[Hydroxy(3,7,11-trimethyl-2,6,10-dodecatrienyl)amino]- 2-oxoethyl]phosphonic acid, disodium salt A. (E,E)-(2-Tetrahydropyranyloxy)-(3,7,11-trimethyl-2,6,10-dodecatrienyl)amine Farnesyl bromide (5.1 ml, 18.7 mmol) in DMF (15 ml) was added dropwise to a solution of O-(2-tetrahydropyranyl)-hydroxylamine (3.28 g, 28 mmol) and potassium carbonate (10.3 g, 75 mmol) in DMF (35 ml) at 0° C. The mixture was warmed to room temperature and stirred for 16 hours. The reaction was quenched with LiCl (10%, 150 ml) and extracted with diethyl ether (3×50 mL). The combined organic extracts were washed with LiCl (10%, 2×50 ml), dried (MgSO$_4$), filtered and concentrated under vacuum. The residue was purified by flash chromatography (eluting with 4:1 hexane/ethyl acetate) to afford compound A (3.03 g, 50%).

MS: (M+H)$^+$ 322

B. (E,E)-[2-[2-Tetrahydropyranyloxy-(3,7,11-trimethyl-2,6,10-dodecatrienyl)amino]-2-oxoethyl]-phosphonic acid, diethyl ester Compound B was prepared from compound A and O,O-diethylphosphonoacetate as described for compound A of Example 2, except that no diisopropylethylamine was used.

MS: (M+H)$^+$ 500

C. (E,E)-[2-[Hydroxy(3,7,11-trimethyl- 2,6,10-dodecatrienyl)amino]-2-oxoethyl] phosphonic acid, diethyl ester A solution of p-toluene sulfonic acid monohydrate (0,158 g, 0.80 mmol) and compound B (0.4 g, 0.80 mmol) in ethanol (4 ml) was stirred for 16 hours. The reaction was concentrated under vacuum, the residue dissolved in diethyl ether (50 ml) and washed with NaHCO$_3$ (10%, 50 ml). The aqueous layer was extracted with diethyl ether (2× 50 ml), and the combined organic extracts were dried (MgSO$_4$), filtered and concentrated under vacuum. The residue was purified by flash chromatography (eluting with 3:1 hexane/acetone) to afford compound C (0.25 g, 75%).

MS: (M+H)$^+$ 416

D. (E,E)-[2-[Hydroxy(3,7,11-trimethyl- 2,6,10-dodecatrienyl)amino]-2-oxoethyl] phosphonic acid, disodium salt The title compound was prepared from compound C as described for Example 2.

mp: decomposition above 165° C.

Analysis for C$_{17}$H$_{28}$NO$_5$PNa$_2$–1.18 H$_2$O

Calculated: C, 48.41; H, 7.03; N, 3.26.

Found: C, 48.52; H, 7.32; N, 3.15.

EXAMPLE 11

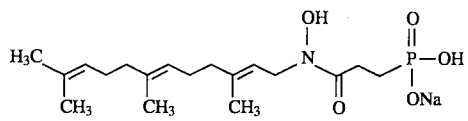

(E,E)-[3-[Hydroxy(3,7,11-trimethyl-2,6,10-dodecatrienyl)amino]- 3-oxopropyl]phosphonic acid, monosodium salt A. (E,E)-[3-[2-Tetrahydropyranyloxy-(3,7,11-trimethyl-2,6,10-dodecatrienyl)amino]-3-oxopropyl]-phosphonic acid, dimethyl ester Compound A was prepared from compound A of Example 10 and O,O-dimethylphosphonopropionate as described for compound compound B of Example 10.

MS: (M+H)$^+$ 486

B. (E,E)-[3-[Hydroxy(3,7,11-trimethyl- 2,6,10-dodecatrienyl)amino]-3-oxopropyl]phosphonic acid, dimethyl ester Compound B was prepared from compound A as described for compound C of Example 10.

MS: (M-H)$^-$ 401

C. (E,E)-[3-[Hydroxy(3,7,11-trimethyl- 2,6,10-dodecatrienyl)amino]-3-oxopropyl] phosphonic acid, monosodium salt The title compound was prepared from compound B as described for Example 2. Chromatography on CHP-20P gel (eluting sequentially with water and 70% aqueous methanol afforded the title compound, mp: 133°–142° C. with decomposition.

Analysis for C$_{18}$H$_{31}$NO$_5$PNa–0.7 H$_2$O

Calculated: C, 52.98; H, 8.00; N, 3.43.

Found: C, 53.02; H, 8.24; N, 3.39.

EXAMPLE 12

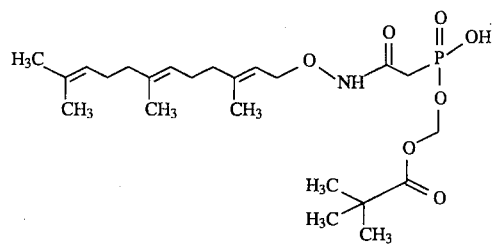

(E,E)-[2-Oxo-2-[[(3,7,11-trimethyl-2,6,10-dodecatrienyl)oxy] amino]ethyl]phosphonic acid, (2,2-dimethyl-1-oxopropoxy)methyl ester, monosodium salt A. (E,E)-[2-Oxo-2-[[(3,7,11-trimethyl- 2,6,10-dodecatrienyl)oxy]amino]ethyl] phosphonic acid, di(tetrabutyammonium) salt The title compound of Example 1 (0.7 g, 1.7 mmol) was dissolved in water (3 ml) and the solution was eluted through a Dowex tetrabutyammonium form ion-exchange column (100 g, 400 ml water) and the eluate was concentrated under vacuum. The residue was dissolved in water (10 ml) and the solution was lyophilized to afford compound A (1.3 g, 89%).

MS: (M+ 2(Bu$_4$N$^+$)–H)$^+$ 842

B. Iodomethylpivalate

Sodium iodide (5.2 g, 34 mmol) was added to a solution of chloromethylpivalate (5 ml, 34 mmol) in acetone (75 ml) and the solution was stirred for 72 hours. The reaction was concentrated under vacuum, dissolved in water (50 ml) and extracted with diethyl ether (3×50 ml). The combined organic extracts were washed with 5% sodium bifsulfate (NaHSO$_4$) (2×50 ml), dried (MgSO$_4$), filtered and concentrated under vacuum to afford compound B (6.7 g, 80%).

MS: (M+NH$_4$)$^+$ 260

C. (E,E)-[2-Oxo-2-[[(3,7,11-trimethyl- 2,6,10-dodecatrienyl)oxy]amino]ethyl] phosphonic acid, (2,2-dimethyl-1-oxopropoxy)methyl ester, monosodium salt Compound B (0.175 g, 0.714 mmol) was added to a solution of compound A (0.40 g, 0.48 mmol) in 1,1,1-trichloroethane (20 ml) and the solution was stirred for 72 hours. The reaction was concentrated under vacuum and purified by a gradient elution on CHP-20P gel (0–50% aqueous acetonitrile). The appropriate fractions were concentrated under vacuum, dissolved in water (3 ml) and eluted through a Dowex Na$^+$ ion-exchange resin (10 g, 100 ml water). The fractions were concentrated under vacuum, dissolved in water (15 ml), millipore filtered and lyophilized to afford the title compound (0.12 g, 51%), mp: 108°–112° C.

Analysis for C$_{23}$H$_{39}$NO$_7$PNa–0.39 H$_2$O

Calculated: C, 54.97; H, 7.98; N, 2.79.

Found: C, 54.90; H, 7.97; N, 2.86.

EXAMPLE 13

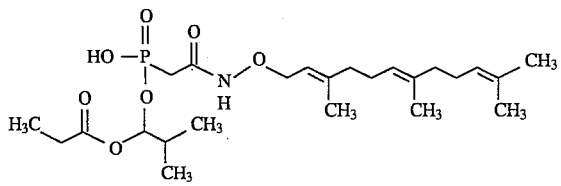

(E,E)-[2-Oxo-2-[[(3,7,11-trimethyl-2,6,10-undecatrienyl)oxy] amino]ethyl]phosphonic acid, 2-methyl- 1-(1-oxopropoxy)propyl ester, monosodium salt A. (E,E)-[2-Oxo-2-[[(3,7,11-trimethyl- 2,6,10-undecatrienyl)oxy]amino]ethyl] phosphonic acid, 2-methyl-1-(1-oxopropoxy)propyl ester, monomethyl ester HCl (1N, 50 ml) was added to the monomethyl ester, monosodium salt of Example 1 (0.70 g, 1.8 mmol; see compound C of Example 1) and the solution extracted with dichloromethane (4×50 ml). The combined organic extracts were dried (MgSO$_4$), filtered and concentrated under vacuum to afford the monoacid (0.66 g). (1-Chloro-2-methyl-propyl)propionate (0.51 g, 3.1 mmol) was added to a solution of the monoacid (0.66 g, 1.8 mmol) and silver carbonate (0.736 g, 2.67 mmol) in acetonitrile (25 ml) and stirred at room temperature for 16 hours. The reaction mixture was concentrated under vacuum and the residue was purified by flash chromatography (eluting with 2:1 hexane/acetone) to afford compound A (0.344, 39%).

MS: (M+H)$^+$ 502

B. (E,E)-[2-Oxo-2-[[(3,7,11-trimethyl- 2,6,10-undecatrienyl)oxy]amino]ethyl]phosphonic acid, 2-methyl-1-(1-oxopropoxy)propyl ester, monosodium salt Tetrabutylammonium chloride hydrate (0.19 g 0.68 mmol) was added to a solution of compound A (0.34 g, 0.68 mmol) in 1,1,1-trichloroethane (14 ml) and heated to reflux for 7 hours. The reaction was concentrated under vacuum and passed through a Dowex Na$^+$ ion exchange column, eluting with 10% aqueous acetonitrile. The appropriate fractions were concentrated under vacuum and the residue was purified on CHP-20P gel (gradient elution 0–65% aqueous acetonitrile). The appropriate fractions were concentrated under vacuum, the residue dissolved in water (10 ml), millipore filtered and lyophilized to afford the title compound (0.11 g, 24%), mp: 58°–66° C.

Analysis for C$_{24}$H$_{41}$NO$_7$PNa–0.46 H$_2$O
Calculated: C, 55.67; H, 8.16; N, 2.71.
Found: C, 55.60; H, 8.20; N, 2.78.

EXAMPLE 14

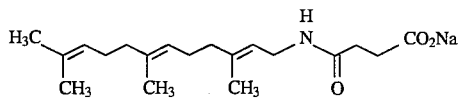

4-Oxo-4-[(3,7,11-trimethyl-2,6,10-dodecatrienyl)amino]-butanoic acid, monosodium salt A. 4-Oxo-4-[(3,7,11-trimethyl-2,6,10-dodecatrienyl)amino]-butanoic acid, methyl ester Carbomethoxypropionyl chloride (0.099 ml, 0.78 mmol) was added to a solution of farnesylamine hydrochloride (0.2 g, 0.78 mmol) in THF (1.5 ml). To the mixture was added diisopropylethylamine (0.34 ml, 1.9 mmol) and the reaction was stirred for 16 hours. The mixture was quenched with HCl (1N, 10 ml) and extracted with ethyl acetate (3× 40 ml). The combined extracts were dried (MgSO$_4$), filtered and concentrated under vacuum. Flash chromatography (3:1 hexane/ethyl acetate) afforded compound A (0.25 g, 98 %).

TLC: R$_f$=0.59 (1:1 hexane/ethyl acetate, visualization by PMA)

B. 4-Oxo-4-[(3,7,11-trimethyl-2,6,10-dodecatrienyl)amino]-butanoic acid, monosodium salt Sodium hydroxide (1N, 0.86 ml, 0.86 mmol) was added to a solution of compound A (0.193 g, 0.58 mmol) in methanol (3 ml). The mixture was stirred 16 hours and concentrated under vacuum, and the residue was chromatographed on a column of CHP- 20 gel (eluting sequentially with water (200 ml), aqueous methanol (50%, 200 ml) and methanol (100 ml)) to afford the title compound (0.18 g, 91%), mp: 175°–180° C. (decomposition).

Analysis for C$_{19}$H$_{30}$NO$_3$Na–0.25 H$_2$O
Calculated: C, 65.58; H, 8.84; N, 4.03.
Found: C, 65.51; H, 9.11; N, 3.92.

EXAMPLE 15

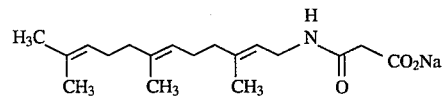

3-Oxo-3-[(3,7,11-trimethyl-2,6,10-dodecatrienyl)amino]-propanoic acid, monosodium salt A. 3-Oxo-3-[(3,7,11-trimethyl-2,6,10-dodecatrienyl) amino]-propanoic acid, ethyl ester Compound A was prepared from ethyl malonyl chloride and farnesylamine hydrochloride as described for compound A of Example 14.

TLC: R$_f$=0.66 (1:1 hexane/ethyl acetate, visualization by PMA)

B. 3-Oxo-3-[(3,7,11-trimethyl-2,6,10-dodecatrienyl) amino]-propanoic acid, monosodium salt The title compound was prepared from compound A as described for Example 14, mp 190°–193 ° C. (decomposition).

Analysis for C$_1$H$_{28}$NO$_3$Na –0.50 H$_2$O
Calculated: C, 63.89; H, 8.64; N, 4.14.
Found: C, 63.88; H, 8.65; N, 4.08.

EXAMPLE 16

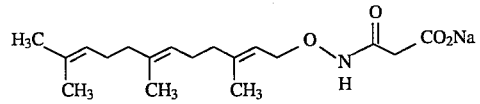

3-Oxo-3-[[(3,7,11-trimethyl-2,6,10-dodecatrienyl)oxy] amino]propanoic acid, monosodium salt A. 3-Oxo-3-[[(3,7,11-trimethyl-2,6,10-dodecatrienyl)oxy] amino]propanoic acid, monoethyl ester Compound A was prepared from ethylmalonyl chloride and compound A from Example 1 as described for compound A from Example 14.

TLC: R$_f$=0.62 (1:1 hexane/ethyl acetate, visualization by PMA)

B. 3-Oxo-3-[[(3,7,11-trimethyl-2,6,10-dodecatrienyl)oxy] amino]propanoic acid, monosodium salt The title compound was prepared from compound A as described for Example 14. Chromatography on SP-207 gel eluting sequentially with water and 50% aqueous methanol afforded the title compound, mp 160°–163° C. (decomposition).

Analysis for C$_{18}$H$_{28}$NO$_4$Na –0.72 H$_2$O
Calculated: C, 60.34; H, 8.28; N, 3.91.

Found: C, 60.18; H, 8.21; N, 4.07.

EXAMPLE 17

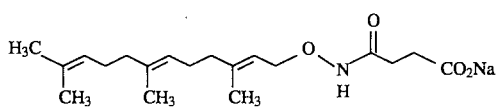

(E,E)-4-Oxo-4[[(3,7,11-trimethyl-2,6,10-dodecatrienyl)oxy] amino]butanoic acid, monosodium salt A. 4-Oxo-4-[(3,7,11-trimethyl-2,6,10-dodecatrienyl)amino]-butanoic acid, methyl ester Compound A was prepared from carbomethoxypropionyl chloride and Compound A from Example 1 as described for compound A from Example 14.

TLC $R_f$=0.79 (1:1 hexane/ethyl acetate, visualization by PMA)

B. (E,E)-4-Oxo-4[[(3,7,11-trimethyl-2,6,10-dodecatrienyl)oxy] amino]butanoic acid, monosodium salt The title compound was prepared from compound A as described for Example 14. Chromatography on SP-207 gel eluting sequentially with water and 20% aqueous methanol (50%) afforded the title compound, mp 166°–168° C.

Analysis for $C_{19}H_{30}NO_4Na$ −0.18 $H_2O$
Calculated: C, 62.91; H, 8.44; N, 3.86.
Found: C, 62.96; H, 8.39; N, 3.81.

EXAMPLE 18

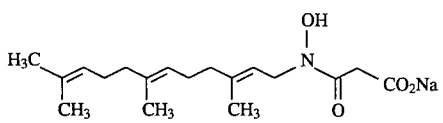

(E,E)-3-[Hydroxy(3,7,11-trimethyl-2,6,10-dodecatrienyl)-amino]- 3-oxopropanoic acid, monosodium salt A. (E,E)-3-[Tetrahydropyranyloxy(3,7,11-trimethyl- 2,6,10-dodecatrienyl)-amino]-3-oxopropanoic acid, methyl ester Compound A was prepared from compound A of Example 10 and ethyl malonyl chloride as described for compound A from Example 14.

TLC: $R_f$=0.33 (4:1 hexane/ethyl acetate, visualization by PMA)

B. (E,E)-3-[Hydroxy(3,7,11-trimethyl-2,6,10-dodecatrienyl)-amino]- 3-oxopropanoic acid, methyl ester Compound B was prepared from compound A as described for compound C of Example 10.

TLC: $R_f$=0.45 (2:1 hexane/ethyl acetate, visualization by PMA)

C. (E,E)-3-[Hydroxy(3,7,11-trimethyl-2,6,10-dodecatrienyl)-amino]- 3-oxopropanoic acid, monosodium salt The title compound was prepared from compound B as described for Example 14. Chromatography on SP-207 gel eluting sequentially with water, 30% aqueous methanol, 60% aqueous methanol and 80% aqueous methanol afforded the title compound, mp bubbling at 125° C. and continuing until decomposition above 150° C.

Analysis for $C_{18}H_{28}NO_4Na$ −0.4 $H_2O$
Calculated: C, 61.31; H, 8.23; N, 3.97.
Found: C, 61.46; H, 8.50; N, 3.80.

EXAMPLE 19

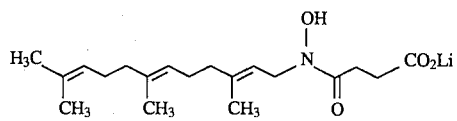

(E,E)-4-[Hydroxy(3,7,11-trimethyl-2,6,10-dodecatrienyl)amino]- 4-oxobutanoic acid, monolithium salt A. (E,E)-4-[Tetrahydropyranyloxy(3,7,11-trimethyl- 2,6,10-dodecatrienyl)amino]-4-oxobutanoic acid, ethyl ester Compound A was prepared from compound A of Example 10 and carbomethoxypropionyl chloride as described for compound A from Example 14, with chromatography using 8:1 hexanes:acetone.

TLC: $R_f$=0.33 (4:1 hexane/acetone, visualization by PMA)

B. (E,E)-4-[Hydroxy(3,7,11-trimethyl-2,6,10-dodecatrienyl)amino]- 4-oxobutanoic acid, ethyl ester Compound B was prepared from compound A as described for compound C of Example 10.

TLC: $R_f$=0.51 (2:1 hexane/ethyl acetate, visualization by PMA)

C. (E,E)-4-[Hydroxy(3,7,11-trimethyl-2,6,10-dodecatrienyl)amino]- 4-oxobutanoic acid, monolithium salt The title compound was prepared from compound B as described for Example 14, using lithium hydroxide, mp: 133°–136° C.

Analysis for $C_{19}H_{30}NO_4Li$ −0.35 $H_2O$
Calculated: C, 65.25; H, 8.85; N, 4.00.
Found: C, 65.23; H, 9.04; N, 4.02.

EXAMPLE 20

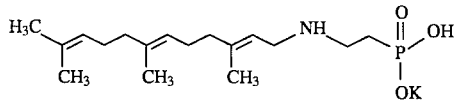

(E,E)-[2-[(3,7,11-Trimethyl-2,6,10-dodecatrienyl)amino] ethyl]phosphonic acid, monopotassium salt A. (E,E)-[2-[(3,7,11-Trimethyl-2,6,10-dodecatrienyl)-amino] ethyl]phosphonic acid, diethyl ester A solution of 617 mg (2.79 mmol) of farnesyl amine in 12 mL of methanol under argon was treated with 430 μL (2.79 mmol) of diethyl vinylphosphonate, and the resultant mixture was stirred for four hours at room temperature and 45 hours at 50° C. The solvent was removed under reduced pressure to obtain 1.06 g of crude compound A. TLC Silica gel (9:0.5:0.5 n-propanol:concentrated ammonia:water) Rf=0.51

B. (E,E)-[2-[((1-Oxo-2,2,2-trifluoro)ethyl)( 3,7,11-trimethyl-2,6,10-dodecatrienyl)amino] ethyl]phosphonic acid, diethyl ester A solution of 1.00 g of crude compound A and 20 mL of distilled dichloromethane at 0° C. under nitrogen was treated with 905 μL (5.2 mmol) of diisopropylethylamine and 550 μL (3.9 mmol) of trifluoroacetic anhydride, and the resultant mixture was stirred for two hours at 0° C. and one hour at room temperature. The solution was diluted with 150 mL of ether, washed with 20 mL of NaHCO$_3$ and 20 mL of brine, dried over MgSO$_4$, and evaporated. Flash chromatography on silica, eluted with 1:1 ethyl acetate:petroleum ether provided 860 mg (67%) of compound B as yellow oil.

TLC Silica gel (1:1 ethyl acetate:hexane) Rf=0.13

C. (E,E)-[2-[(3,7,11-Trimethyl-2,6,10-dodecatrienyl)-amino] ethyl]phosphonic acid, monopotassium salt A mixture of 823 mg (1.71 mmol) of compound B and 340 μL (2.56 mmol) of collidine in 10 mL of distilled dichloromethane at 0° C. under argon was treated with 565 μL (4.28 mmol) of bromotrimethylsilane, and the resultant mixture was stirred for one hour at 0° C. and for 24 hours at room temperature. The solvent was removed under vacuum, the residue was dissolved in a mixture of 7 mL of methanol and 6.85 mL (6.85 mmol) of 1 M KOH, and the solution (~pH 13) was stirred at room temperature for 24 hours. After evaporation, the residue was dissolved in 5 mL of water and the solution was applied to a column of HP-20 packed in water. The column was eluted with a forerun of water (300 mL), followed by a gradient created by the gradual addition of acetonitrile to water. Appropriate factions were combined and lyophilized, and the resulting white powder was further dried at high vacuum over phosphorus pentoxide to provide 447 mg (71%) of the title compound.

Analysis Calculated for $C_{17}H_{31}NO_3P$ (MW 367.518) C. 55.56; H, 8.50; N, 3.81; P, 8.43.

Found: C, 54.91; H, 8.60; N, 3.71; P, 8.2.

EXAMPLE 21

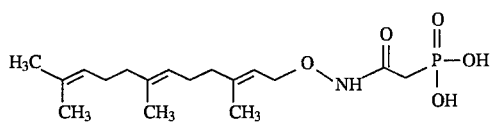

(E,E)-[2-Oxo-2-[[(3,7,11-trimethyl-2,6,10-dodecatrienyl)oxy] amino]ethyl]phosphonic acid, disodium salt A. N-((3,7,11-Trimethyl-2,6,10-dodecatrienyl) oxy)-phthalimide To a stirred solution of 3.48 g (15.7 mmol) of farnesol, 2.81 g (17.2 mmol) of N-hydroxyphthalimide, and 4.93 g (18.8 mmol) of triphenylphosphine in 45 ml of THF at room temperature was added 2.7 ml (17.2 mmol) of diethyl azodicarboxylate in 5 ml of THF over 15 minutes, in an exothermic reaction. After 2 hours at room temperature, the solvent was evaporated, the solids triturated with 1:1 ether/hexane and the slurry filtered to remove insoluble solids. The filtrate was flash chromatographed on silica gel, eluted with 10:90 ethyl acetate/hexane, to provide 4.57 g (79%) of Compound A as white flakes, m.p. 56.5°–57.5° C.

B. ((3,7,11-Trimethyl-2,6,10-dodecatrienyl) oxy)amine

Methylhydrazine (1.3 ml, 24.5 mmol) was added to a solution of 1.72 g (4.65 mmol) of Compound A in 25 ml of ethanol under argon. After stirring for 40 minutes at room temperature, 10 ml of 1M NaOH was added and the ethanol was evaporated. The residue was extracted with ether, and the ether layer was washed with 1M NaOH, water and brine, dried (MgSO₄) and evaporated to provide 1.1 g (99%) of Compound B as a colorless oil.

C. O,O-Diethylphosphonoacetate

A solution of triethyl phosphonoacetate (4.5 g, 20 mmol) in 15 ml of ethanol was treated with 21 ml (21 mmol) of 1M NaOH and the mixture was stirred for 3 hours at room tempertaure. The ethanol was evaporated, the residue was acidified with 1M KHSO₄ and the aqueous layer was washed with three-100 ml portions of dichloromethane. The organic layer was washed with brine, dried (MgSO₄) and evaporated to provide 3.18 g (81%) of Compound C as a colorless liquid.

D. (E,E)-[2-Oxo-2-[[(3,7,11-trimethyl-2,6,10-dodecatrienyl)oxy] amino]ethyl]phosphonic acid, diethyl ester To a solution of 992 mg (5.05 mmol) of Compound C in 15 ml of dry THF under argon was added 818 mg (5.05 mmol) of 1,1-carbonyldiimidazole. After 100 minutes at room temperature, 1.07 g (4.51 mmol) of Compound B in 7 ml of THF was added dropwise over 20 minutes at room temperature. After 1 hour, the solvent was evaporated and the residue dissolved in ether which was washed with 1 M HCl, water, saturated NaHCO₃ and brine. The organic layer was dried (MgSO₄) and evaporated to provide 1.95 g (100%) of pure Compound D as a colorless liquid.

E. (E,E)-[2-Oxo-2-[[(3,7,11-trimethyl-2,6,10-dodecatrienyl)oxy] amino]ethyl]phosphonic acid, disodium salt A solution of 428 mg (1.03 mmol) of Compound D in 4 ml of dry dichloromethane under argon was treated with 0.34 ml (2.58 mmol) of collidine, followed by 0.61 ml (4.64 mmol) of bromotrimethylsilane. The reaction was stirred for 3 hours at room temperature, the solvent was evaporated and the residue held under vacuum. The residue was dissolved in 3 ml of 1M NaOH, adjusted to pH 12 and lyophilized. The crude solid was purified by MPLC on CHP₂₀P gel, eluting with a gradient that ranged from pure water to 75:25 acetonitrile/water. Pure fractions were combined, the acetonitrile evaporated and the aqueous residue was lyophilized to provide 364 mg (88%) of the title compound as a white powder.

TLC Silica gel (6:3:1 propanol/concentrated ammonium hydroxide/water $R_f$=0.5 IR (KBr) 1644, 1448, 1085, 975 cm⁻¹. ¹H NMR (D₂O) δ5.34 (t, 1H, J=7.5 Hz), 5.01 (m, 2H), 4.34 (d, 2H, J=7.5 Hz), 2.40 (d, 2H, J=18.7 Hz), 1.80–2.10 (m, 8H), 1.64 (s, 3H), 1.56 (s, 3H), 1.50 (s, 3H), 1.48 (s, 3H) ppm. MS (FAB, +ions) 382 (M+2H-Na), 404 (M+H).

Analysis Calculated for $C_{17}H_{28}NO_5PNa_2$+0.34 H₂O: C, 49.86; H, 7.06; N, 3.42; P, 7.56. Found: C, 50.05; H, 7.05; N, 3.21; P, 7.29.

What is claimed is:

1. A compound of the formula

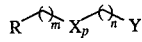

or an enantiomer, diastereomer, pharmaceutically acceptable salt, prodrug or solvate thereof, wherein:

X is —ONR¹C(O)— or —N(OH)C(O)—;

Y is —CO₂R², —SO₃R² or —P(O)(OR²)(R³);

R is alkyl, substituted alkyl, alkenyl, substituted alkenyl, alkenylene or aryl;

R³ is —(O)ₜR⁴;

R¹, R² and R⁴ are each independently hydrogen, alkyl, aryl or aralkyl;

m and n are each independently 0 or an integer from 1 to 5; and t is 0 or 1.

2. A compound of claim 1, wherein X is —ONHC(O)— or —NOHC(O)—.

3. A compound of claim 1, wherein Y is —CO₂R² or —P(O) (OR²) (R³).

4. A compound of claim 1, wherein Y is —CO₂H, —P(O)(OH)(OH) or —P(O)(OH)(CH₃).

5. A compound of claim 1, wherein

Y is —CO₂R² or —P(O) (OR²) (R³);

R is alkenylene;

R¹, R² and R⁴ are each hydrogen or lower alkyl; and n is 1 or 2.

6. A compound of claim 1, wherein

X is —ONHC(O)— or —NOHC(O)—;

Y is —CO₂H, —P(O) (OH) (OH) or —P(O) (OH)(CH₃);
R is alkenylene; and
n is 1 or 2.

7. A compound of claim 1, selected from the group consisting of:
(E,E)-[2-Oxo-2-[[(3,7,11-trimethyl-2,6,10-dodecatrienyl)oxy] amino]ethyl]phosphonic acid,
(E,E)-[3-[[(3,7,11-Trimethyl-2,6,10-dodecatrienyl)oxy] amino]-3-oxypropyl]-phosphonic acid,
(E,E)-[2-Methyl-[(3,7,11-trimethyl-2,6,10-dodecatrienyl)oxy] amino]-2-oxoethyl]-phosphonic acid,
[2-[(Dodecyloxy)amino]-2-oxoethyl]phosphonic acid,
(E)-[2-[[(3,3,7,11-Tetramethyl-6,10-dodecadienyl)oxy)-amino]-2-oxoethyl]-phosphonic acid,
(E,E)-Methyl-[2-oxo-2-[[(3,7,11-trimethyl-2,6,10-dodecatrienyl)oxy] amino]ethyl]-phosphinic acid,
(E,E)-[2-[Hydroxy(3,7,11-trimethyl-2,6,10-dodecatrienyl)amino]-2-oxoethyl] phosphonic acid,
(E,E)-[3-[Hydroxy(3,7,11-trimethyl-2,6,10-dodecatrienyl)amino]-3-oxopropyl] phosphonic acid,
3-Oxo-3-[[(3,7,11-trimethyl-2,6,10-dodecatrienyl)oxy] amino]propanoic acid,
(E,E)-4-Oxo-4[[(3,7,11-trimethyl-2,6,10-dodecatrienyl)oxy] amino]butanoic acid,
(E,E)-3-[Hydroxy(3,7,11-trimethyl-2,6,10-dodecatrienyl)-amino]-3-oxopropanoic acid,
(E,E)-4-[Hydroxy(3,7,11-trimethyl-2,6,10-dodecatrienyl)amino]-4-oxobutanoic and
(E,E)-[2-Oxo-2[[(3,7,11-trimethyl-2,6,10-dodecatrienyl)oxy] amino]ethyl]phosphonic acid.

* * * * *